United States Patent [19]

Young et al.

[11] Patent Number: 4,686,479

[45] Date of Patent: Aug. 11, 1987

[54] APPARATUS AND CONTROL KIT FOR ANALYZING BLOOD SAMPLE VALUES INCLUDING HEMATOCRIT

[76] Inventors: Chung C. Young, 145 Buckskin Dr., Weston, Mass. 02193; Robert L. Coleman, 65 Indian Head Rd., Framingham, Mass. 01701; Sheila M. Sullivan, 71 Marlboro St., Wollaston, Mass. 02170; John F. Grimes, 30 Fenelon Rd., Framingham, Mass. 01701; Ferdnand Baumeister, One Winchester St., Nashua, N.H. 03063; Robert MacIndoe, 18 Prunier St., P.O. Box 299, Linwood, Mass. 01525; Lou Catalano, 31 Frankland Rd., Ashland, Mass. 01721; Pat Coppola, Five Cedar St., Burlington, Mass. 01803; Fred Spaziani, 41 Fair Oaks Dr., Lexington, Mass. 02173; Guy Rodomista, Nine Blueberry Hill Rd., Natick, Mass. 01760; James E. Fowler, 54 Barnard Ave., Watertown, Mass. 02172

[21] Appl. No.: 757,573

[22] Filed: Jul. 22, 1985

[51] Int. Cl.$^4$ .............................................. G01N 27/02
[52] U.S. Cl. .................................... 324/439; 324/450; 204/1 T; 204/400; 204/419
[58] Field of Search ...................... 324/439, 71.1, 71.4, 324/450; 204/1 T, 403, 406, 409, 411, 412, 416, 400, 418–420; 436/8, 70; 422/61, 68, 99; 73/864.86; 339/91 R, 255 R

[56] References Cited

U.S. PATENT DOCUMENTS

| | | | |
|---|---|---|---|
| 3,556,950 | 7/1966 | Dahms | 204/409 X |
| 3,997,420 | 12/1976 | Buzza | 324/439 X |
| 4,092,232 | 5/1978 | Zetter | 204/195 P |
| 4,096,047 | 6/1978 | Hale et al. | 204/400 X |
| 4,202,747 | 5/1980 | Buzza et al. | 204/400 X |
| 4,452,682 | 6/1984 | Takata et al. | 204/400 X |
| 4,484,135 | 11/1984 | Ishihara et al. | 324/439 X |
| 4,632,485 | 12/1986 | Brown et al. | 339/91 R |

OTHER PUBLICATIONS

Okada and Schwan, IRE, Transactions on Medical Electronics, "An Electrical Method to Determine Hematocrits", Jul. 1960, pp. 188–192.

Primary Examiner—Reinhard J. Eisenzopf
Assistant Examiner—Jack B. Harvey

[57] ABSTRACT

Hematocrit level of a blood sample is measured by flowing the sample along a liquid flow path and using electrodes in the flow path to obtain electrical signals representative of the sample's electrical conductivity and of the concentration of an ion species in the path, either before or after the sample measurement. Electrical signals are obtained for standardizing solution conductivity and ion species concentration. A tentative sample hematocrit value is derived from the sample and standardizing conductivity signals. Then the tentative hematocrit value is corrected with reference to the sample and standardizing ion concentration signals and to the known standardizing solution ion concentration value. A control solution of the ion species at known concentration is used for evaluating the hematocrit detection apparatus; the solution also includes an ion activity enhancing agent. A removable septum assembly is used in a blood sample component measuring apparatus in which at least two standardizing solutions are introduced into the flow path. The septum assembly comprises: (a) chamber-defining members, which define a plurality of chambers, the members being permanently attached to each other; and (b) flexible septa positioned between the chambers, each septum having a slit, the slits being aligned to sealably receive therethrough an elongated probe connected to a flush fluid and each remaining chamber being connected to a standardizing fluid introducing lines, the septum assembly being removably attached as a unit to the apparatus which includes means for releasably attaching the septum assembly in position to receive the probe through the slits.

30 Claims, 16 Drawing Figures

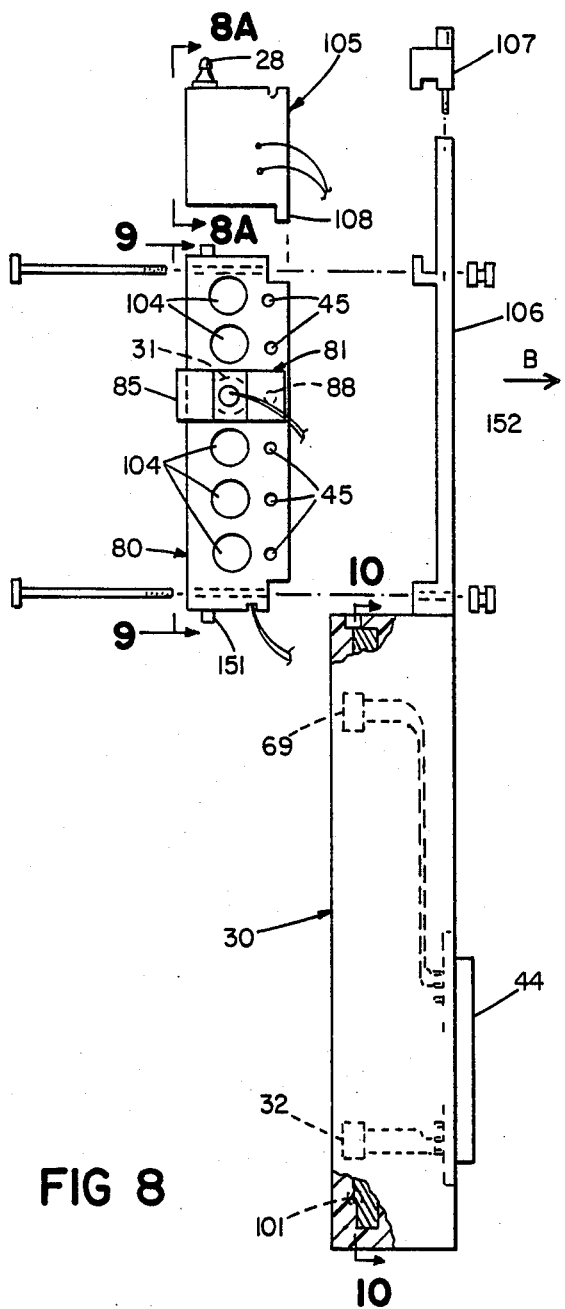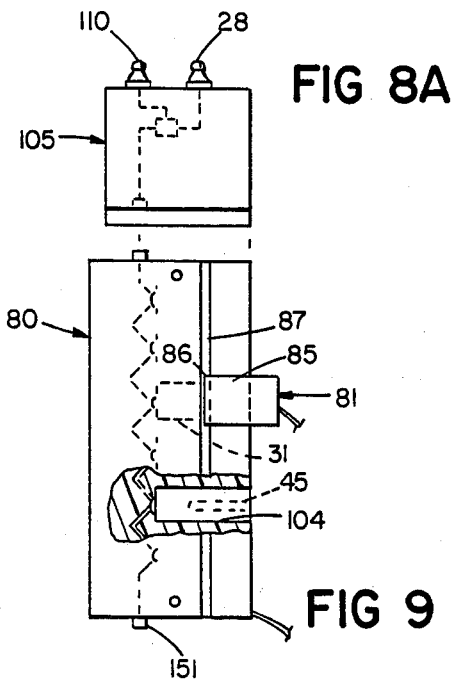

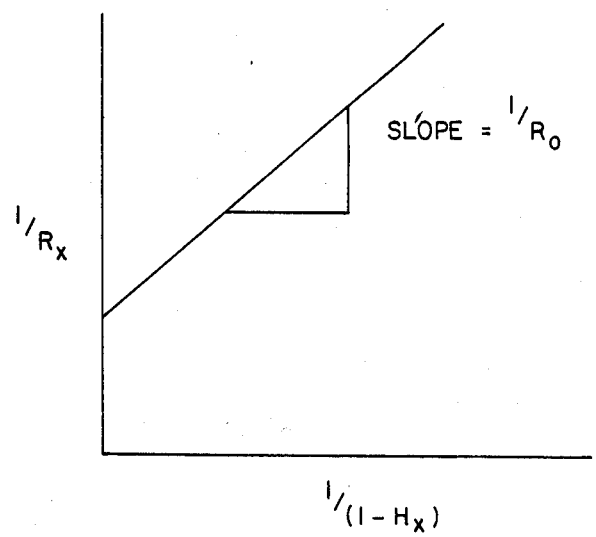
FIG 12A
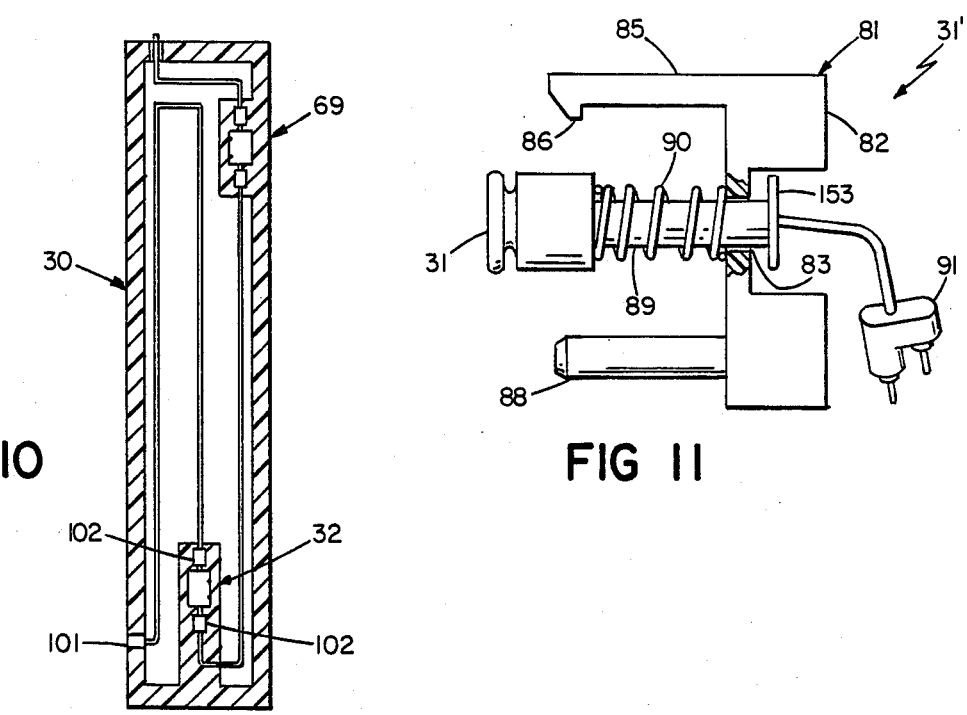
FIG 10
FIG 11

4,686,479

APPARATUS AND CONTROL KIT FOR ANALYZING BLOOD SAMPLE VALUES INCLUDING HEMATOCRIT

BACKGROUND OF THE INVENTION

This invention relates to blood analyzers used to measure various components in a blood sample, for example in medical diagnosis and research.

The ratio of the volume of packed red blood cells from a whole blood sample to the total sample volume is a useful measurement for diagnosing anemia and other disease conditions. That ratio usually is referred to as the "hematocrit ratio" or the "hematocrit value", and it is usually determined by centrifuging a whole blood sample to separate cells from plasma. It is known that, all other things being constant, the conductivity of a blood sample varies as a function of its hematocrit value, but other blood components, notably electrolytes, influence conductivity significantly, and the conductivity of those components must be accurately accounted for if a reliable hematocrit value is to be derived from conductivity readings.

Automated equipment for determining blood components, such as electrolyte concentration or dissolved blood gas partial pressures, often involve the use of electrodes positioned along a flow path. When whole blood is introduced in the flow path, the electrodes provide a reading of the desired blood characteristic. Currently, electrodes are available to provide electrical signals representative of various blood components such as sodium ion concentration ("[$Na^+$]"), potassium ion concentration ("[$K^+$]"), calcium ion concentration ("[$Ca^+$]"), hydrogen ion concentration ("pH"), partial pressure attributed to $O_2$ ("$PO_2$"), and partial pressure attributed to $CO_2$ ("$PCO_2$"). From time to time it may be necessary to replace various components of a blood analyzer flow path, such as an electrode or a rubber inlet septum. Moreover, particularly in analyzers with a small, tortuous flow path having dead spots, whole blood may clot, resulting in lost time from shut-down, disassembly, cleaning, re-assembly, and re-starting of the apparatus.

SUMMARY OF THE INVENTION

In one aspect of the invention, the hematocrit level of a blood sample is measured by flowing the sample along a liquid flow path and using means in the flow path to obtain electrical signals representative of the sample's electrical conductivity and of the concentration of an ion species in the sample. Standardizing solution is introduced in the same flow path, either before or after the sample measurement. The standardizing solution has a known ion species concentration and a conductivity indicative of a known equivalent hematocrit value; "equivalent" hematocrit value is used in this application to mean the hematocrit level of a blood sample having a conductivity corresponding to that of the standardizing solution, even though the standardizing solution contains no whole blood cells and has an actual hematocrit value of 0. Electrical signals are obtained for standardizing solution conductivity and ion species concentration. A tentative sample hematocrit value is derived from the sample and standardizing conductivity signals, with reference to the known equivalent standardizing hematocrit value. Then the tentative hematocrit value is corrected with reference to the sample and standardizing ion concentration signals and to the known standardizing solution ion concentration value.

In preferred embodiments of the method, an external validation of the apparatus is provided from time to time by introducing a control solution into the flow path, which is described below in connection with the third aspect of the invention. Also in preferred embodiments, conductivity of solutions in the flow path is obtained by: (a) providing electrodes in the flow path coupled to a constant current AC circuit via a transformer; (b) applying an AC signal from the AC circuit to the electrodes via the transformer; and (c) detecting reflected impedance in the AC circuit. The method comprises: (a) obtaining the electrical signals representative of standardizing conductivity and standardizing ion concentration; (b) storing signals representative of the known standardizing equivalent hematocrit value and the known standardizing ion concentration value; (c) obtaining the electrical signals representative of sample concentration and standardizing ion concentration; (d) comparing the sample and the standardizing ion concentration signals with reference to the stored known standardizing value signal, to derive a signal representative of sample ion concentration value; (e) comparing the sample and the standardizing conductivity signals with reference to the stored standardizing hematocrit value signal to derive a signal representative of a tentative sample hematocrit value; and (f) correcting the tentative sample hematocrit value signal with reference to the sample ion concentration signal and the stored standardizing ion concentration value signal. Preferred ion species for use in the method are $Na^+$ or $Cl^-$.

The invention also features, in another aspect, apparatus for determining hematocrit value in a blood sample comprising: (1) means for providing a fluid flow path; (2) means in the flow path for providing an electrical signal representative of the conductivity of liquid passing along the flow path; (3) means in the flow path for providing a signal representative of the concentration of an ion species in liquid passing along the flow path; (4) means for introducing the blood sample into the flow path to obtain a signal representative of sample conductivity and of sample ion species concentration; (5) means for introducing into the flow path a standardizing solution having a known concentration of an ion species and having a conductivity representative of a known equivalent hematocrit value; (6) means for deriving a signal representative of a tentative sample hematocrit value from the sample conductivity signal, with reference to the standardizing conductivity signal, and to the standardizing equivalent hematocrit value; and (7) means for correcting the tentative sample hematocrit value with reference to the standardizing and sample ion concentration signals and to the known standardizing ion concentration.

In preferred embodiments the apparatus includes: (a) means for storing either the sample or the standardizing conductivity signal, and means for comparing the conductivity signals with reference to the known standardizing equivalent hematocrit value to generate a signal representative of the tentative sample hematocrit value; and (b) means for correcting the tentative sample hematocrit value signal including means for storing either the standardizing or the sample ion concentration signal and comparing the ion concentration signals with reference to the known standardizing ion concentration value. The apparatus comprises at least two standardizing solutions, each of which has a conductivity indicative of a known equivalent hematocrit value and a known ion concentration. The conductivity measuring means comprises electrodes in the flow path, a constant current AC circuit coupled to the electrodes via a transformer and means for detecting the reflected impedance in the AC circuit. Specifically, the conductivity signal-generating means comprises: (1) a first transformer for coupling the AC circuit to the electrodes; and (2) a second transformer for maintaining constant current in the AC circuit; means establishing a loop between the electrodes and means, connected in the loop between the second transformer and the electrodes, selected to compensate for inherent capacitance at the electrode/sample interface. The apparatus comprises an ion species sensing electrode positioned in the flow path and connected via an electrical output circuit connected to the input of a multiplexer, the impedance detecting means also being connected to the input of the multiplexer, the multiplexer having an output means connected via an analog-to-digital converter to a means for storing and comparing signals, and to the means for correcting sample conductivity.

In a third aspect the invention features a control solution kit for evaluating the hematocrit detection apparatus. The solution comprises an aqueous solution of the ion species (e.g. $Na^+$ or $Cl^-$) at a known concentration; and an ion activity enhancing agent (e.g. a polyol selected from glycerol and polyalkyl glycols). The solution has a conductivity representative of a known equivalent hematocrit level, and both the ion concentration and the equivalent hematocrit value preferably are within physiological ranges (e.g., $[Na^+]$ is between 130–150 mM, and hematocrit is between 40 and 55%).

The hematocrit measurement aspects of the invention provide rapid, accurate highly automated measurements of the hematocrit level, without the need for the analyzer user to store whole blood standards.

In a fourth aspect the invention features an electrode clip for use in apparatus for determining the concentration of a component of a blood sample, the apparatus comprising a means defining a sample flow path, means in the flow path generating an electrical signal representative of the component concentration, and means for moving fluid along the path under pressure, the flow path comprising an electrode block having an opening for receiving an electrode to contact fluid in the path, the opening communicating with the flow path. The signal generating means comprises an electrode attached to a clip means for resiliently and removably forcing the electrode into the block opening to effectively seal the opening against pressure leakage.

In preferred embodiments of the electrode clip, the clip means comprises an electrode support slidably inserted through a retainer, the retainer comprising a means for cooperatively engaging the electrode block, and the clip means further comprises a biasing means for biasing the electrode support away from the retainer against the block. The retainer comprises a deflectable latch element cooperatively engaging the electrode block.

The electrode clip enables an operator to quickly remove or insert any one electrode using a simple, one-handed operation in an area of the apparatus where there is little space available for manual manipulations.

In a fifth aspect the invention features a removable septum assembly for use in a blood sample component measuring apparatus in which at least two standardizing solutions are introduced into the flow path. The septum assembly comprises: (a) chamber-defining members, which define a plurality of chambers, the members being permanently attached to each other; and (b) flexible septa positioned between the chambers, each septum having a slit, the slits being aligned to sealably receive therethrough an elongated probe connected to the apparatus flow path, one chamber being connected to a flush fluid and each remaining chamber being connected to a standardizing fluid (liquid or gas) introducing means, the septum assembly being removably attached as a unit to the apparatus which includes means for releasably attaching the septum assembly in position to receive the probe through the slits.

In preferred embodiments of the septum assembly, the releasable attachment means comprises a post on the base of the septum assembly and a means on the apparatus for cooperatively engaging the post, the engaging means comprising a pair of elongated resilient spring means spaced to receive and releasably engage the post therebetween. Each septum comprises an annular ridge positioned radially outwardly of, and concentrically with, the slit to seal against a chamber-defining member. Each chamber-defining member comprises an inlet means, and the standardizing fluid introducing means comprises an integral standardizing fluid-flow-path manifold connector having a plurality of outlets, each of which is positioned and sized to removably seal to an inlet means. Each inlet means comprises a cylindrical inlet positioned in a recess in the chamber-defining member, and the manifold connector is cooperatively sized and shaped to fit within those recesses.

The septum assembly is particularly advantageous in that it is a single unit that can be pre-tested by the manufacturer before use, and it does not require customer assembly. The part is relatively inexpensive to produce and therefore it can be disposed of as the septa became worn. The use of a manifold enables a quick connection to the septum assembly and reduces the risk of misconnections.

In a sixth aspect, the invention features an electrode block assembly apparatus for determining the concentration of a component of a blood sample having a means defining a sample flow path, means in the flow path generating an electrical signal representative of the component concentration, and means for driving fluid along the path. The flow path comprises a heater path means, an electrode block path means connected immediately downstream of the heater path means, and a reference path means connected immediately downstream of the electrode path means. The heater path means, the electrode path means, and the reference path means are connected as a single unit, which is removable from the apparatus.

In preferred embodiments of the sixth aspect, the heater path means, the electrode path means, and the reference path means comprise attachment means allowing them to be severed from each other, whereby, one path means can be replaced by removing the unit, removing the path means from the unit, and replacing the path means.

Advantageously, various parts of the analyzer such as the septum assembly, the electrodes, and the electrode block are designed so that when they become worn out, or clogged, they can be replaced easily and quickly, minimizing down time on the analyzer.

Other features and advantages of the invention will be apparent from the following description of the preferred embodiment and from the claims.

DESCRIPTION OF THE PREFERRED EMBODIMENT

We first briefly describe the drawings.

I. Drawings

FIG. 8 is a side view of the holder assembly of FIG. 6 with parts exploded, broken away, and in section.

FIG. 8A is a view of the reference block of the assembly of FIG. 6, taken along 8A—8A of FIG. 8.

FIG. 9 is a view along 9—9 of FIG. 8 with parts broken away and in section.

FIG. 10 is a view, in section, along 10—10 of FIG. 8.

FIG. 11 is a plan side view of an electrode clip for use in the assembly of FIG. 6.

FIG. 12A is a graph of the reciprocal of resistivity versus 1/(1-hematocrit value).

II. Structure

Figure 1:
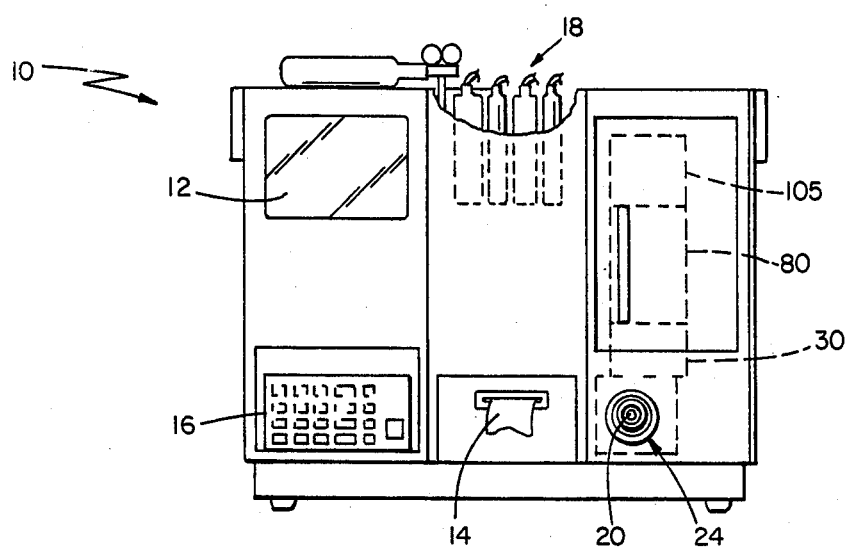
FIG. 1 is a front view of a blood analyzer.
Figure 2:
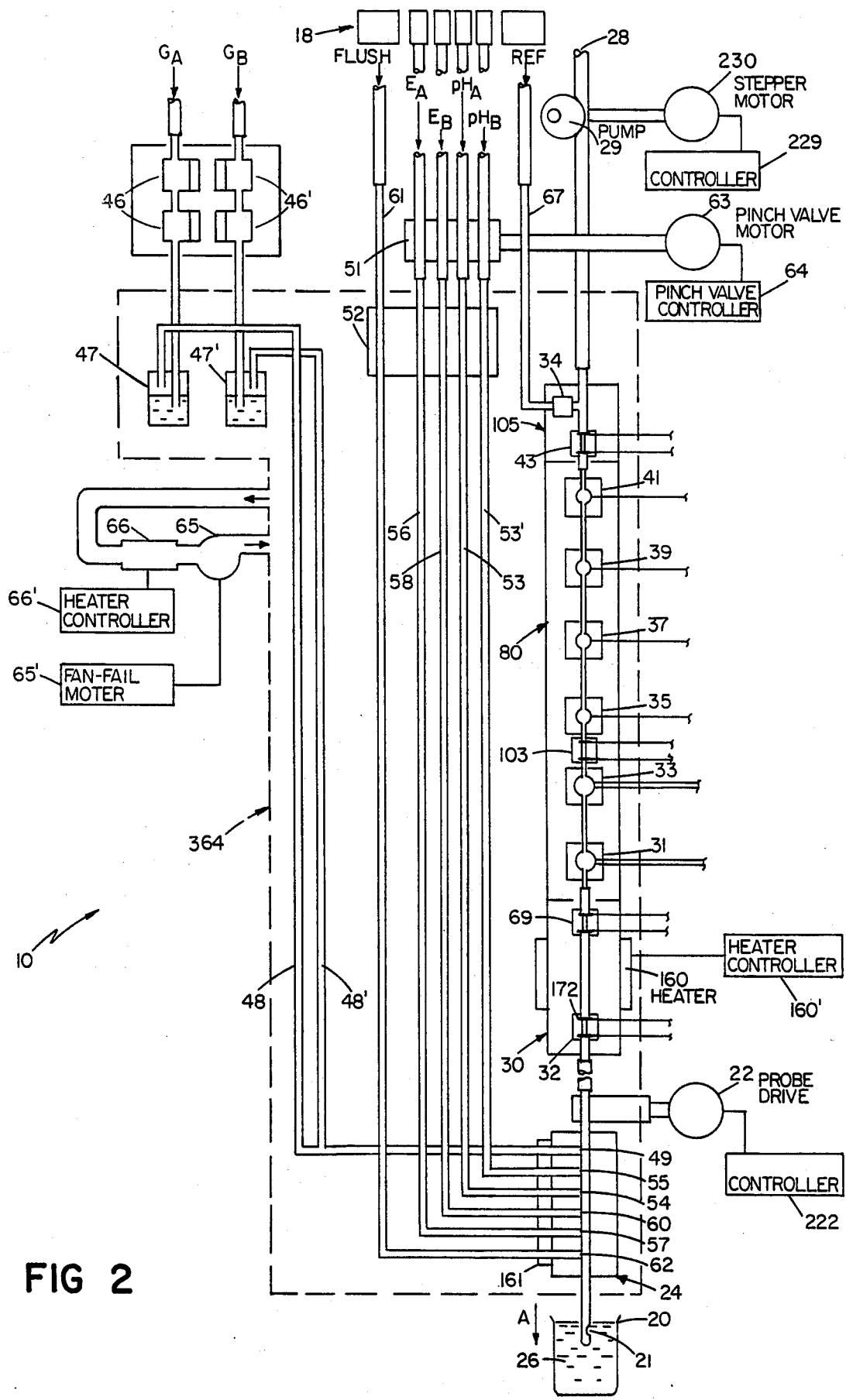
FIG. 2 is a diagrammatic representation of the fluid flow path and some of the electrical components of the analyzer of FIG. 1.

Analyzer 10 of FIG. 1 provides for measurement of the concentrations of certain electrolytes and gases in a small (e.g. less than about 0.25 ml) sample of whole blood that has been treated (e.g. with heparin) to prevent coagulation. Specifically, the treated sample is drawn from its container through a probe 20, along a sample flow path, and out a waste outlet 28 (FIG. 2). Readings of sample $PO_2$, $PCO_2$, $[Na+]$, $[K+]$, $[Ca++]$, and pH are provided on a C.R.T. display 12 and a tape printer 14. The same flow path includes means to provide a measurement and readout of the sample hematocrit value.

The above measurements are performed as described in greater detail below, using electrodes and associated components that yield an electric signal representative of the characteristic being measured. In order to ascribe a value to the signal, the electrodes are standardized periodically with standard gases from replaceable cylinders and with standard fluids from a replaceable fluid pack 18 whose components and operation are also described below. The operation of the electrodes and standardizing apparatus is controlled by a computer 130 (FIG. 13) in response to a control program and to the operator's entries on keypad 16.

A. Sample Flow Path

As illustrated in FIG. 2, probe 20 is a hollow elongated metal tube (e.g. stainless steel) having a fluid inlet 21 at one end and connected at the other end to a fluid flow path. A probe drive motor 22, controlled by controller 222, moves the probe longitudinally through septum assembly 24, while the probe outlet remains in communication with the fluid flow path. The furthest longitudinal extension of the probe in the direction of arrow A is shown in FIG. 2, with probe inlet 21 positioned outside the septum assembly, immersed in a sample 26 that is to be drawn through the inlet and along the flow path.

FIG. 2 diagrams the sample flow path through an electrode assembly (best shown in FIGS. 6-10 and described in greater detail below) that includes: a heater block 30 heated by a resistance heater 160; a series of six electrodes, 31, 33, 35, 37, 39, and 41 in an electrode block 80 that enable generation of signals representative of $PO_2$, $PCO_2$, pH, $[Ca++]$, $[K+]$, and $[Na+]$, respectively; and a reference block 105. The external, mechanical configuration of the electrodes is described below; the electrochemical principles and composition of the electrodes are conventional. From electrode block 80, the sample flows to waste outlet 28. The fluid flow is drawn along the path by a peristaltic pump 29, driven by stepper motor 230 under the control of controller 229.

Along the flow path, there are air detectors to sense conductivity changes representative of the change from air to liquid, thereby providing an indication of air/liquid transitions and thus to signal changes from one fluid to another and to verify sample and standard positioning. Specifically, one air detector 32 is positioned in heating block 30, and a detector 69 located in heater block 30 serves as a hematocrit level detector as described in greater detail below. A third air detector 103 is located in the electrode block. Finally, a clamp electrode 43 is positioned upstream from waste outlet 28 to connect to circuitry that minimizes the common mode voltage range and thereby improves the sensitivity and stability of the electrode measurement.

B. Standard Flow Paths

The analyzer has been designed particularly to flow the various standard fluids through the flow path and to flush the flow path, while minimizing any opportunity for contamination between standards, or between a standard and a blood sample. As best shown in FIG. 2, the standards are assigned to specific flow paths and chambers in septum assembly 24, and from there, the standards flow through the above-described sample flow path to waste outlet 28. The various standards and their flow paths are:

(1) $G_A$, which is a source of gas having known $PO_2$ and $PCO_2$ composition, connected via metering solenoid valves 46 (sold by Lee Company, Westbrook, Conn.) to a humidifier 47 and thence, via line 48 to chamber 49 of the septum assembly 24.

(1) $G_A$, which is similar to $G_A$, having different $PO_2$ and $PCO_2$ composition, thereby enabling standardization of those two electrodes; $G_B$ communicates with chamber 49 of septum assembly 24 via solenoid valves 46', humidifer 47' and line 48'.

(3) $pH_A$, a liquid of known pH that flows via line 53 to chamber 54 of septum assembly 24;

(4) $pH_B$, a standard similar to $pH_A$, having a pH different from that of $pH_A$, that flows via line 53' to septum assembly chamber 55. Standard $pH_B$ has a total conductivity indicative of a known equivalent hematocrit value. As explained in greater detail below, a solution having a known conductivity can be treated as the equivalent of a whole blood sample having a specific "equivalent hematocrit value."

(5) $E_A$, an electrolyte standard having a known $[Na^+]$, $[K^+]$, and $[Ca^{++}]$ and also having a total conductivity indicative of a known equivalent hematocrit value different from the value of $pH_B$; $E_A$ flows via line 56 to septum assembly chamber 57.

(6) $E_B$, an electrolyte standard having a known $[Na^+]$, $[K^+]$, and $[Ca^{++}]$, different from those of $E_A$; standard $E_B$ flows via line 58 to septum assembly chamber 60.

The composition of the various standard solutions is given in more detail below.

Each of lines 53, 53', 56, and 58 flows through a pinch valve 51 that is controlled by D.C. motor 63, and controller 64 to shut those lines selectively and separately when they are not in use. Each of lines 53, 53', 56, and 58 flows through a preheater to warm the standard solutions somewhat before they enter the heating block 30. A flush line 61 bypasses pinch valve 51 and flows through preheater 52 to septum assembly chamber 62. Lines 48, 48', 61, 56, 58, 53, and 53' terminate in a rigid multi-plug connector 161 that is adapted to cooperate with the septum assembly 24 so that all of the lines can be connected simultaneously. Specifically, connector 161 is shaped to fit within recesses of the septum assembly surrounding each inlet to a septum assembly chamber and, when connector 161 is properly positioned, an outlet from each of the lines 48, 53, 53', 56, 58, and 61 removably seals to the appropriate septum inlet by overlapping it.

A high molarity reference solution (Ref) flows through line 67 where it contacts reference electrode 34, and from there into the above sample flow path between clamp electrode 43 and waste outlet 28. The use of an open reference junction (i.e., a junction that is not enclosed in a membrane) enables the use of a low pressure flow for reference solution, and thereby reduces any possibility of contamination of the sample flow path or the electrode sensors by reference solution. The dotted line 64 indicates the region of the analyzer bathed in air from heater 66 driven by fan 65 (connected to controller 66' and fan-fail monitor 65') to stabilize temperature.

Three specific features of the analyzer are discussed below in greater detail: septum assembly 24; electrode assembly 68 (FIG. 6); and hematocrit detection via conductivity detector 69.

C. Septum Assembly

Referring to FIGS. 3, 4, 4A, and 5, removable septum assembly 24 has chambers 49, 54, 55, 57, and 60, and 62 which are separated by rubber septa 70 (FIG. 3) that have been slit to receive probe 20 and to form a seal around the probe as it is extended through the assembly. The septum assembly enables the analyzer to automatically draw one or more of the reference fluids along the sample flow path without contamination of future samples. As best shown in FIGS. 3, 4, 4A, and 5, the assembly includes an end mounting unit 71 and a plurality of central septa supports 72, each of which has a radial inlet 373 connecting with an axial central channel 74. A cylindrical rubber septum 70 seats in a cylindrical cavity 75 of the end mounting unit 71 and each central unit 72.

Figure 4:
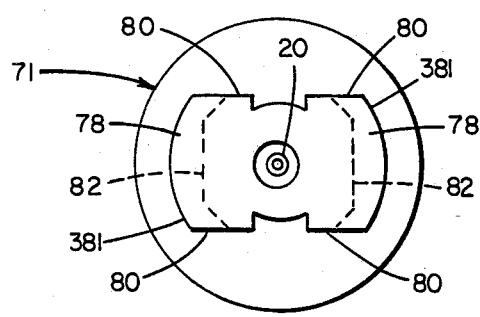
FIG. 4 is a view along 4—4 of FIG. 5.
Figure 4A:
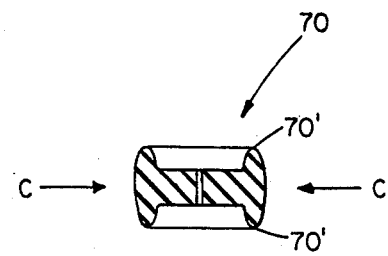
FIG. 4A is a section of a septum from the septum assembly of FIG. 3.
Figure 3:
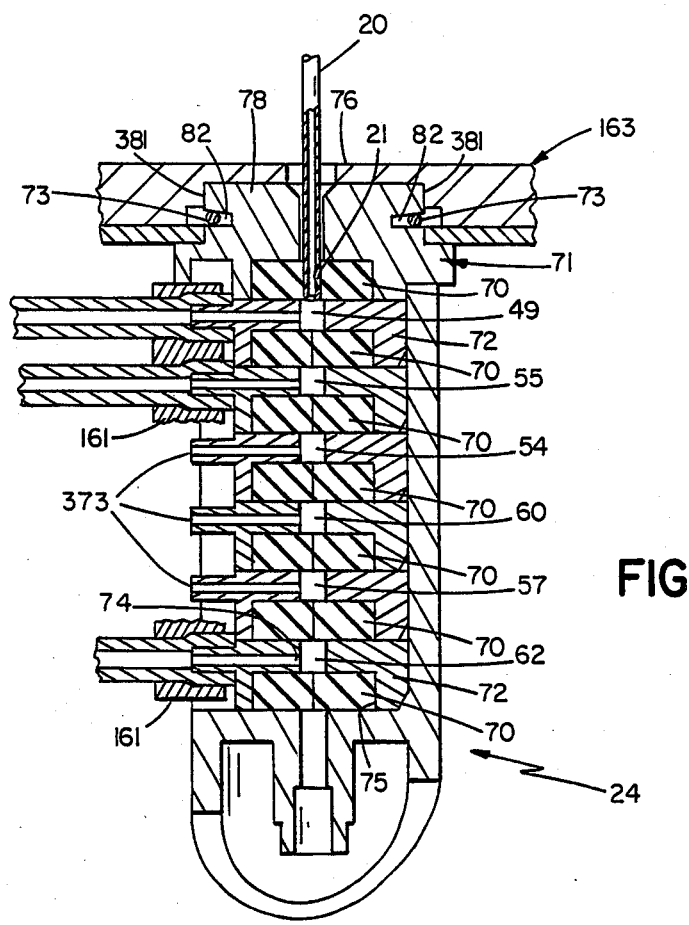
FIG. 3 is a side view, in section, of the septum assembly and septum mounting plate of the analyzer of FIG. 1.

FIG. 4A shows a septum 70 in cross-section, free from the stresses it experiences in the assembly. Specifically, very small (e.g. 0.010") annular rims 70' around the periphery of each side of septum 70 are designed so that, when the septum is seated, cavity 75 having a restrained diameter, it is subjected to moderate radial squeezing (arrow C) sealing at the ridge, so sealing is enhanced, and leakage around the probe is reduced. In this way, the septum design provides an adequate seal without the need for a tight fit that causes friction and wear as the probe moves.

The assembly is produced by aligning all of the units with unslit septa in place, and an external sleeve 77 is then placed over the sub-assembly. The assembly then is ultrasonically welded together. After ultrasonic welding, a knife is passed through the central channels 74 to form small slits in each septum 70. Because the septa are placed in alignment first, and then slit, the size of the slits can be minimized and alignment is ensured, to reduce wear on the septa from repeated movement of the probe through them, thereby lengthening the useful life of assembly 24.

Figure 5:
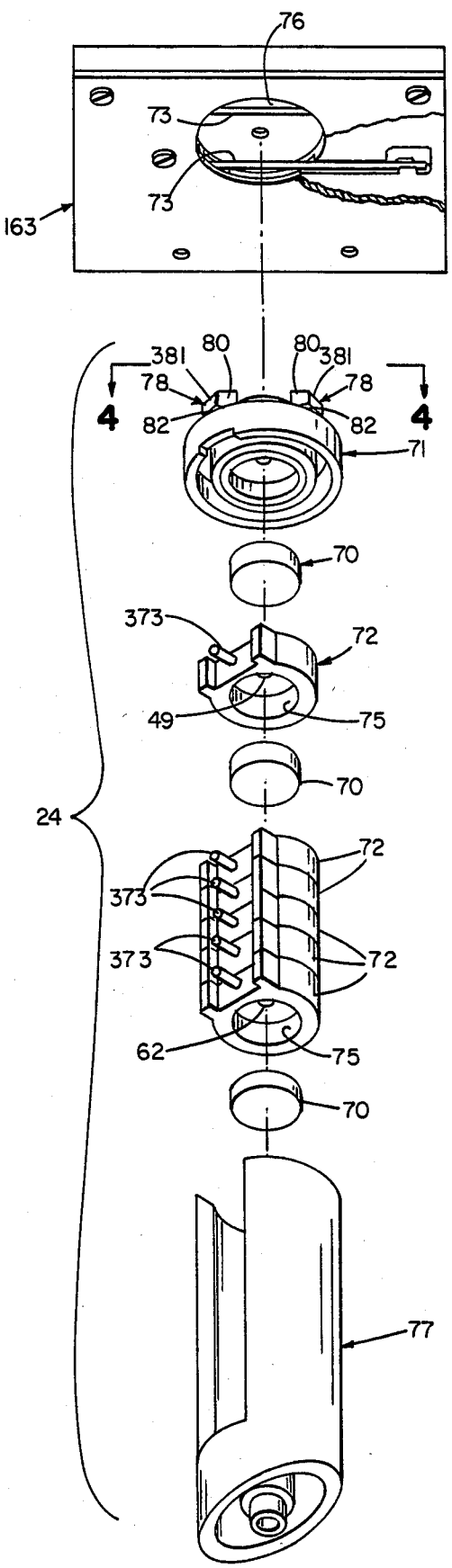
FIG. 5 is an exploded view, with parts broken away, of the septum assembly and mounting plate of FIG. 3.
Figure 7:
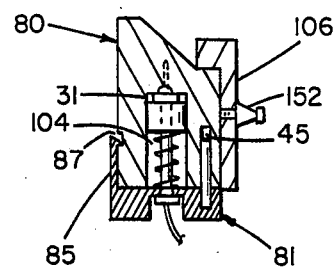
FIG. 7 is a view, in section, along 7—7 of FIG. 6.
Figure 6:
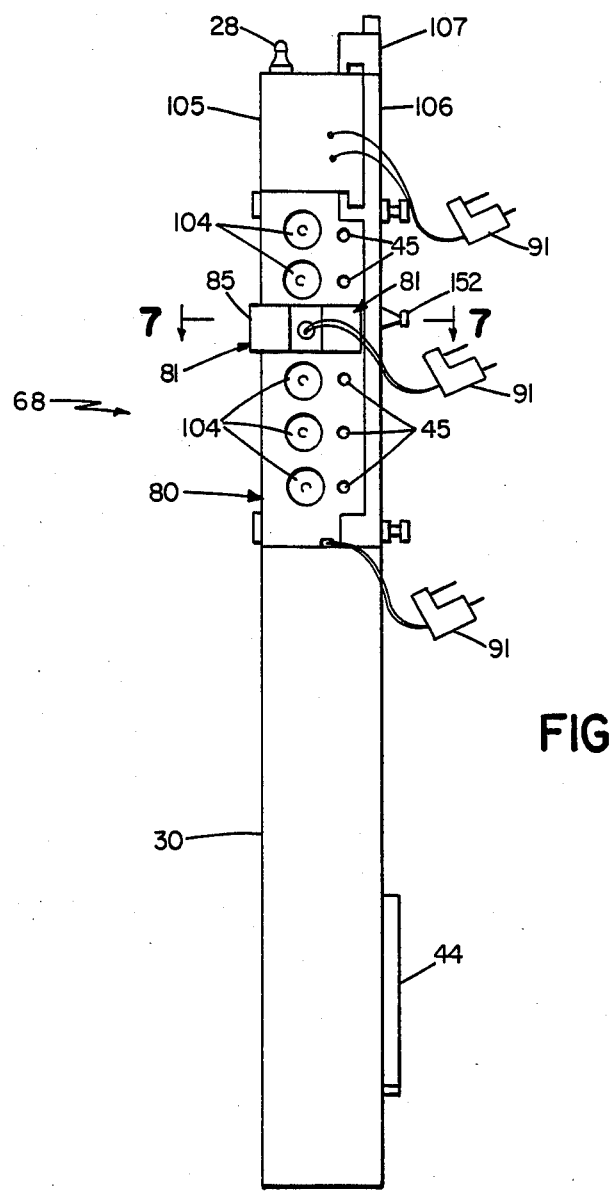
FIG. 6 is a side view of the electrode holder assembly of the analyzer of FIG. 1.

As the slits in septa 70 become worn, the seal between chambers in the assembly can be affected, and the possibility of contamination is increased, so that it is necessary to replace the septum assembly from time to time. To facilitate removal of the assembly from the analyzer, end unit 71 is designed to rotatably engage and disengage a spring-loaded latch on mounting plate 163 of analyzer 10 as shown in FIG. 5. Specifically, a cylindrical recess 76 on plate 163 the face of analyzer 10 includes two thick, resilient parallel wires 73, spaced apart at a preset distance. End unit 71 of assembly 24 includes two seating posts 78 that have parallel flat sides 80 positioned to fit between wires 73. Two flanges 381 of posts 78 are generally flat, with slightly rounded corners, and define generally straight parallel grooves 82 spaced apart a distance that is very slightly less than the distance between wires 373. To insert the septum assembly, its end 71 is inserted in recess 76 in an initial position with sides 80 parallel to, and positioned between, wires 73, and then the assembly is rotated in either direction to engage wires 73 in grooves 82. At $\frac{1}{8}$ turn, the wires are resiliently forced apart by the shoulders of grooves 82 creating a position of instability such that, a slight movement away from the $\frac{1}{8}$ turn position will release the biasing force of the wires to re-establish a stable position. At $\frac{1}{4}$ turn from the initial position, the wires seat in the grooves and lock the assembly in place. A $\frac{1}{4}$ turn in either direction releases the assembly.

Once assembly 24 is inserted, manifold connector 161 is forced into place so that each of the various standardizing lines sealingly overlaps the proper inlet on the septum assembly as shown in FIG. 4.

D. Electrode Assembly

Figure 13:
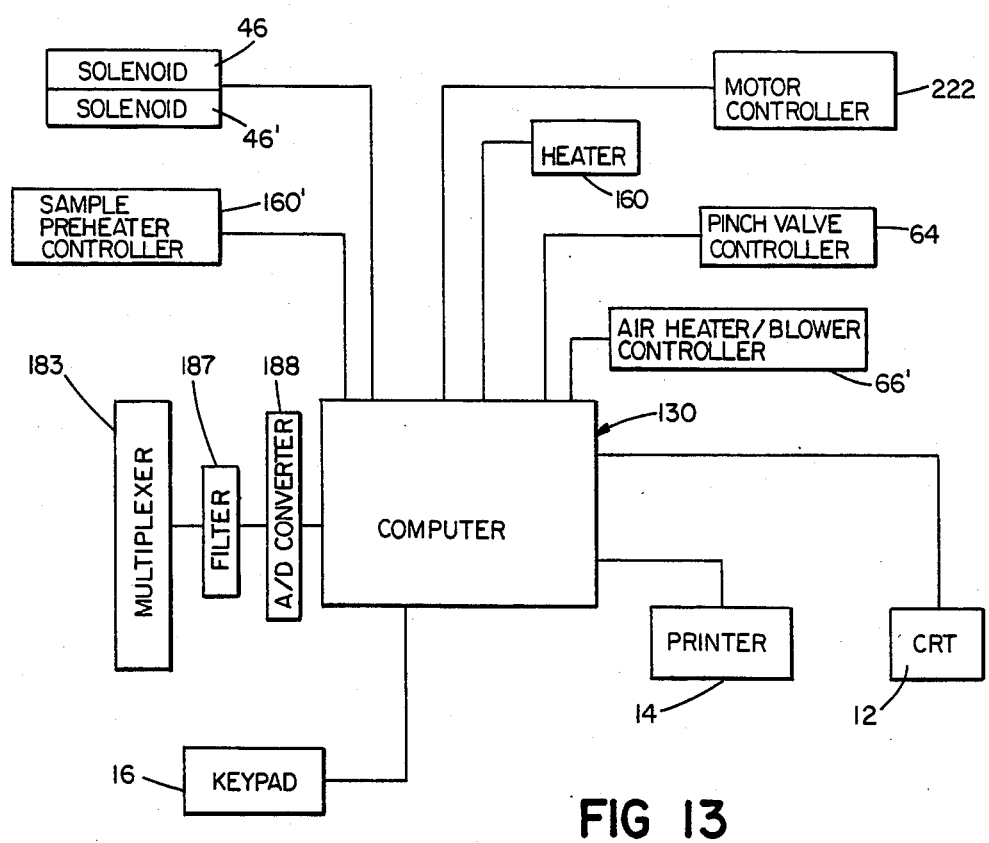
FIG. 13 is a diagrammatic representation of the electrical functions of the analyzer of FIG. 1.

The fluid flow path exiting the probe communicates with an electrode assembly shown in FIGS. 6–11. The path enters heating block 30 through inlet 101 (FIG. 10) and follows a circuitous route through stainless steel tubing to allow heat transfer from the heating block. Block 30 includes air detector 32 having a pair of electrodes 102 that are spaced apart in a chamber having passivated (e.g. $HNO_3$ etched stainless steel) walls. Electrodes 102 are connected to a reflected impedance detector that is driven by an AC source and generates a signal to be converted to digital signal to control the probe via computer 130 (FIG. 13). From air detector 32, the fluid passes to hematocrit detector 69, described in greater detail below.

As shown in FIG. 8, the connection between heater block 30 and electrode block 80 is formed by a small piece of Tygon (TM Norton Co., Worcester, Mass.) tubing 151 that fits over the ends of stainless steel tubing from the flow path of each block; the Tygon tubing fits within countersinks in the respective blocks surrounding the ends of the stainless tubing. In electrode block 80, the flow path passes over each of electrodes 31, 33, 35, 37, 39, and 41 (FIG. 2) in sequence. Air detector 103 (FIG. 2), which is positioned between electrode 33 and electrode 35, operates as described above regarding detector 32. As shown in FIG. 9, the flow path follows a zig-zag path between wells at the bottom of cylindrical electrode cavities 104 in block 80.

The downstream component of the electrode assembly is a reference block 105 which includes clamp electrode 43 (FIG. 2) and a T connection upstream from it, connecting to reference line 67, allowing reference fluid (Ref.) to be drawn out waste outlet 28. The reference electrode 34 in line 67 serves as a reference for electrodes 35, 37, 39, and 41, (the pH, [Ca++], [K+], and [Na+] electrodes). The two gas electrodes 31 and 33 have internal references.

The flow path has a relatively narrow diameter (e.g. 0.7 mm) and is tortuous as shown in FIG. 9, and therefore clots may form in the path. Conveniently, heater block 30, electrode block 80, and reference block 105 are separate units that can be disassembled and replaced individually, as shown in FIG. 8, when it is necessary to replace one of them or to clean a blood clot from them. Specifically, heater block 30 includes a back plate 106 to which electrode block 80 is bolted. A lipped retainer 107 screws into the top edge of plate 106 and grips a notch in the top of reference block 105; and a lip 108 on the bottom of the rear face of reference block 105 engages a groove in the top of electrode block 80. Electrical connections to the heaters and air detectors of block 30 are made through multi-pin connector 44. Connections to the electrical components of blocks 80 and 105 are made through male connector plugs that allow easy separation of the units. A locator pin 152 extends rearwardly from plate 106 to guide the electrode assembly as it is forced in the direction of arrow B (FIG. 8) into a cooperatively shaped recess in the analyzer. A flow path inlet 109, a reference inlet 110 (FIG. 9), and waste outlet 28 extend from the assembly to be connected to tubing in the analyzer.

It is particularly advantageous that the entire fluid flow path of the electrode assembly (i.e. through the heater, the electrodes and the reference block) can be readily removed and replaced in a short time, removing only two bolts. In that way, when a part of the flow path becomes defective, the flow path can be replaced with an alternate part and the apparatus can be restarted without taking time to cure the defect in the original part. Thus downtime on the apparatus can be significantly reduced merely by maintaining spare flow path parts.

Each of electrodes 31, 33, 35, 37, 39, and 41 is mounted on an individually replaceable unit, one of which (electrode unit 31') is shown in FIG. 11. Electrode unit 31' consists of an electrode-carrying cylinder 89 movably inserted through an opening 83 in the back 82 of a clip 81. Clip 81 has a resiliently deflectable ridge 85 extending from one end, which terminates in a latch 86 sized to engage a groove 87 in block 80. A guide pin 88 extending from clip 81, at the end opposite to latch 85, fits in opening 45 in block 80. Cylinder 89 has a diameter small enough to fit easily within opening 83, and a compression spring 90 is seated between clip 81 and a flange on the cylinder, thus biasing the cylinder into an electrode cavity 104 in block 80. A flange 153 on the rear of cylinder 89 prevents the cylinder from passing through the clip opening 83. The $PCO_2$ electrode 31 is bonded to cylinder 89, and cylinder 89 is hollow to accommodate wiring and (because it is a gas electrode with an internal reference) a reference electrode that electrically connects the electrode to signal-generating apparatus via plug 91.

E. Hematocrit Value Detector

The apparatus provides a rapid, accurate hematocrit-value determination, electronically, without time-consuming, labor intensive centrifuging and visual measurement and without using a whole blood standard. The hematocrit value determination is based on the relationship between a blood sample's electrical conductivity (C) and its hematocrit value (H), which is given the expression $$C = C_o(1-H) \tag{1}$$

where $C_o$ is the conductivity when H=O. The blood analyzer determines the conductivity of the sample by obtaining a resistance signal and comparing it to resistance signals from two reference solutions, each having a different known conductivity. The analyzer includes electrical components to provide a linear signal-to-resistivity relationship in the area of interest, so that the two references are sufficient to establish a value corresponding to the sample resistivity signal.

The electrical conductivity of a blood sample depends on a number of factors in addition to the hematocrit value, notably concentrations of various electrolytes, so any conversion of standard fluid conductivity to hematocrit value necessarily implies concentration levels for such electrolytes. The sample electrolyte concentration may vary enough from those implied standard concentrations to require correction; however, it has been found that, if the sodium concentration implied in the standard is used to correct the actual sample conductivity, the hematocrit value obtained will be accurate within the ranges necessary for blood hematocrit measurements.

In general, assuming a given [Na+] level and given detector geometry, the resistance ($R_x$) is related to hematocrit value as shown in FIG. 12A, where $R_o$ is the resistance at H=0. Thus, $R_x$ can be used to obtain the hematocrit value ($H_x$) of a blood sample using the known resistance ($R_A$) and known hematocrit value ($H_A$) of a standard A by the following equation:

$$R_x - R_A = R_o[1/(1-H_x) - 1/(1-H_A)] \tag{2}$$

where $R_o$ is the resistance at H=O.

In order to determine $R_o$, a second standard having a known equivalent hematocrit value ($H_B$) is needed. One of the pH standards, e.g. $pH_B$, is preferably used for this purpose. By measuring the resistance ($R_B$) of $pH_B$ and the resistance ($R_A$) of $E_A$, $R_o$ can be determined from equation (2). Once $R_o$ is known, and $R_x$ and $R_A$ can be measured, and the sample hematocrit ($H_x$) can be obtained by rearranging equation (2), $H_A$ being known also:

$$1/(1-H_x) = 1/(1-H_A) + (R_x - R_A)/R_o \tag{3}$$

The equivalent hematocrit values of the standards can be determined by standardizing them to actual whole blood standards.

To correct for variations in resistance attributed to variations in [Na+], the true sample hematocrit value ($H_x^*$) can be obtained from $H_x$ using the following relationship:

$$1/(1-H_x^*) = 1/(1-H_x)\cdot(Na_x/Na_{STD}) \quad (4)$$

where $Na_{STD}$ is the [Na+] in standard $E_A$ and $Na_x$ is the sample [Na+].

When operating the analyzer, it is highly desirable to use an external control to confirm the accuracy of the instrument. The external control could be a whole blood sample having very precisely known electrolyte, pH, blood gas and hematocrit levels. However, whole blood is relatively expensive and difficult to handle because it has a short shelf life and is relatively unstable.

For this reason, it is desirable to use a surrogate solution that mimics whole blood sufficiently to serve as a satisfactory control. A stable aqueous buffer having known electrolyte and pH could serve as a control for all readings other than hematocrit. The difficulty in using such a buffer as a hematocrit level control lies in the fact that, at normal physiological ranges, the sodium ion concentration is about 130 mM-150 mM. The conductivity of such a solution provides an equivalent hematocrit value of less than 5%, which is far below the normal range of around 50%.

It is highly desirable to have the equivalent hematocrit value of the control in normal ranges, in part because of the limitations on the linear signal-to-resistance range of the analyzer circuitry. One could try to raise the equivalent hematocrit level of the control by reducing its [Na+], but in so doing, the [Na+] would have to be drastically reduced and therefore the correction required by equation (4) would largely counterbalance any effective increase in the corrected hematocrit value.

This dilemma is resolved by adding an ion activity coefficient enhancer to the aqueous control solution in order to increase the ion activity measured by the [Na+] sensing electrode and to increase the resistance measured by the hematocrit resistance detector. By including such an enhancer in the control solution, the actual [Na+] may remain well below physiological levels, but the [Na+] sensing electrode measures ion activity, and the increased Na+ activity coefficient resulting from the presence of the enhancer will provide a signal equivalent to a physiological [Na+]; thus, the [Na+] correction resulting from equation (4) will not affect the control hematocrit significantly.

Suitable activity coefficient enhancers are polar, water-miscible organic compounds, particularly polyols such as polyethylene glycol, glycerol, and polypropylene glycol. It is possible, using such activity enhancers, to formulate control solutions with [Na+] in the normal range (130 mM-150 mM) and with conductivities characteristic of a sample having a normal hematocrit (40%-55%).

Suitable control solutions have a [Na+] of 20-60 mM, [K+] of 0.5 mM-1.7 mM, [Ca++] of 0.1-0.5 mM, pH of 6.8-7.6 and between 10% and 50% (V/V) of an enhancer such as glycerol. Two specific such control solutions are:

| Control #1 | | Control #2 | |
|---|---|---|---|
| [Na+] = | 52 mM | [Na+] = | 24 mM |
| [K+] = | 1.5 mM | [K+] = | 0.7 mM |
| [Ca++] = | 0.46 mM | [Ca++] = | 0.2 mM |
| pH = | 7.46 | pH = | 7.46 |
| glycerol = | 38% (V/V) | glycerol = | 17% (V/V) |

Suitable pH standards are buffered solutions exemplified by the following:

| | | |
|---|---|---|
| $pH_A$: | $KH_2PO_4$ | 8.695 mM |
| | $Na_2HPO_4$ | 30.430 mM |
| | $NaHCO_3$ | 0.1040 mM |
| | final pH = 7.384 | |
| $pH_B$: | $KH_2PO_4$ | 25 mM |
| | $Na_2HPO_4$ | 25 mM |
| | final pH = 6.840 | |
| | [Na+] = 30-70 mM 950 preferred) | |

Suitable electrolyte standards are exemplified by the following:

| |
|---|
| $E_A$: [Na+] = 120-160 mM (140.0 preferred); [K+] = 4.00 mM; [Ca++] = 1.00 mM |
| $E_B$: [Na+] = 75.0 mM; [K+] = 20.0 mM; [Ca++] = 2.00 |

Suitable gas standards have between 0-25% $O_2$ and 0-15% $CO_2$, the balance being $N_2$.

Sutiable Ref. and flush solutions are well known to those in the art.

Figure 12:
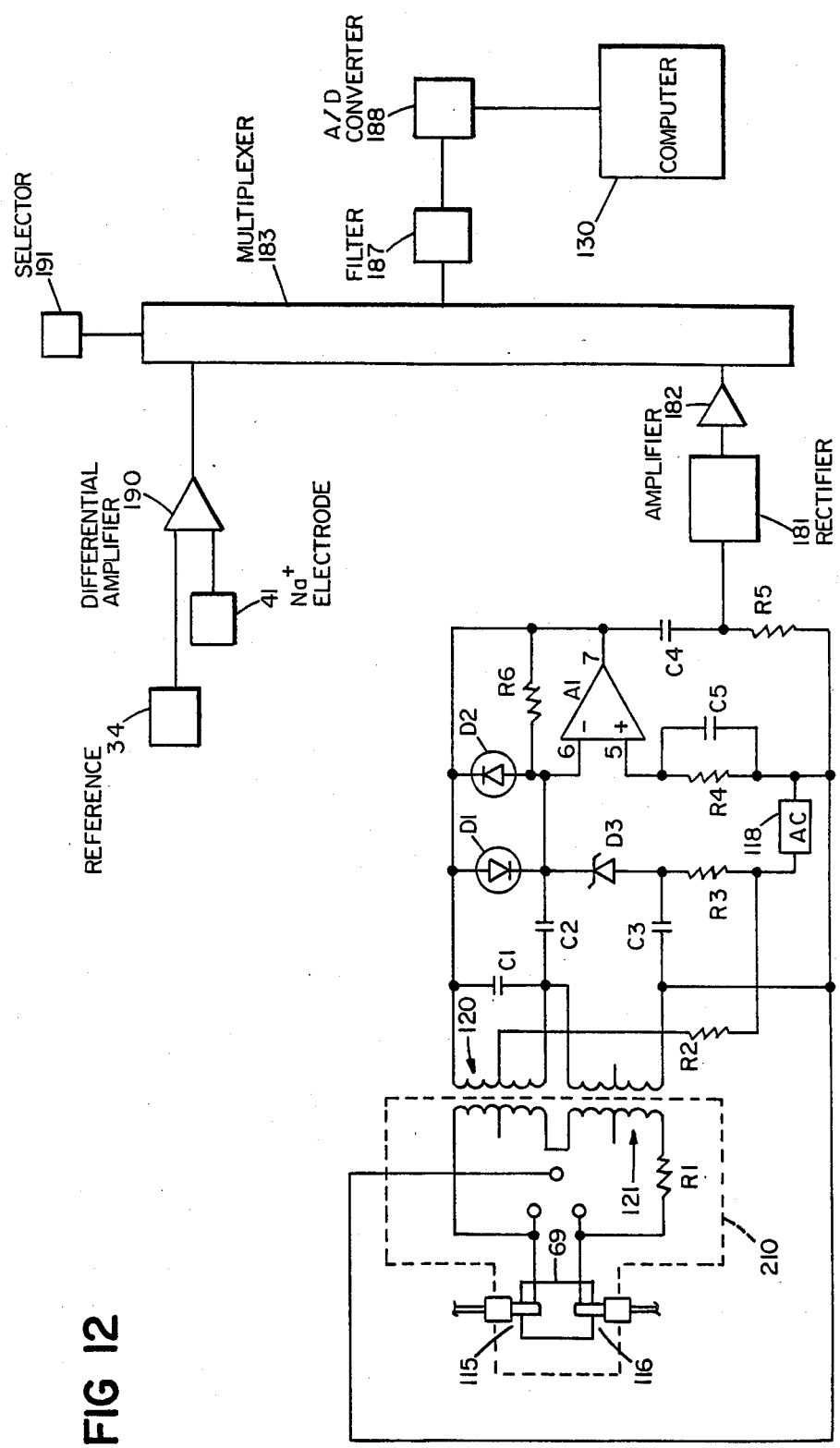
FIG. 12 is a diagrammatic representation of electronic components and functions related to the hematocrit detector of the analyzer of FIG. 1.

Referring to FIG. 12, as a solution passes through hematocrit detector 69, the resistance between electrodes 115 and 116 is measured through a reflected impedance technique in a constant current AC circuit that communicates with electrodes 115 and 116 via transformers 120 and 121. A resistor $R_1$ (typically about 20K ohm) is selected for stability, e.g. to avoid positive feedback due to phase shift from the boundary layer capacitance at the electrodes. The winding ratio on transformer 120 is 1:1, and the winding ratio on transformer 121 is 25:1. The circuitry isolates the AC excitation means and the measuring means from the electrodes, avoiding direct connections, d.c. polarizing effects, and providing the ability to function over a relatively large common mode voltage range at the electrodes. The circuitry also provides a linear signal-to-resistivity relationship over a relatively large range.

As shown more specifically in FIG. 12, a 900 hz constant voltage A/C source 118 is connected to the drive coil of transformer 120. The other coil of transformer 120 is connected to electrode 115 of detector 69. Electrode 116 is connected through resistor $R_1$ to the drive coil of transformer 121 to complete the loop 210 from which electrode impedance is to be communicated to the constant current AC circuit. Transformer 121 provides feedback to maintain constant current in the impedance measuring circuit. The resulting signal from the constant circuit, reflected impedance detecting circuitry, is connected to multiplexer 183 via filtered output, full-wave rectifier 181, and non-inverting amplifier 182. The following table provides values and part numbers for the schematically illustrated components.

TABLE 1

| Component | Value or Part No. |
| --- | --- |
| $R_1$ | 20K ohm |
| $R_2$ | 20K ohm |
| $R_3$ | 300K ohm |
| $R_4$ | 1 M ohm |
| $R_5$ | 100K ohm |
| $R_6$ | 1 M ohm |
| $C_1$ | .0022 micro farad |
| $C_2$ | 10 micro farad |
| $C_3$ | 0.1 micro farad |
| $C_4$ | 0.1 micro farad |
| $C_5$ | 0.1 micro farad |
| $D_1$ | HLMP-1301 (Hewlett Packard) |
| $D_2$ | HLMP-1301 (Hewlett Packard) |
| $D_3$ | 1N 821 A |
| $A_1$ | TL074C (Texas Instrument) |
| Transformer 120 | SP-66 (Triad) |
| Transformer 121 | SP-48 (Triad) |

As also shown in FIG. 12, sodium electrode 41 and reference electrode 34 are connected to differential amplifier 190 to provide a signal representative of [Na$^+$] to multiplexer 183. A selector 191 selects an input signal (e.g. from amplifier 190, amplifier 182, or other circuitry not shown) to be output, through filter 187 and analog-to-digital converter 188, to computer 130, an Intel SBC 80/IOB computer comprising an 8080A CPU microprocessor.

First the standardizing solutions $E_A$ and $E_B$ are circulated through the flow path, and computer 130 stores signals representing their respective conductivities and [Na$^+$], as well as the $H_A$, $H_B$, and $Na_{STD}$ values. When values for $R_A$ and $R_B$ have been determined, together with the known $H_A$, $H_B$, and $Na_{STD}$ values, then the corrected sample hematocrit $H_x^*$ can be derived by measuring $R_x$ and $Na_x$, using computer 130 to perform the above calculations. A suitable program in assembly language for performing those calculations on the 8080A CPU microprocessor is included as an appendix to this application. In the program the hematocrit value is referred to as $(H_{ct})$.

III. Operation

The analyzer is used to measure characteristics of a blood sample. After the apparatus is turned on, the various heaters and blowers are allowed to equilibrate and pump 29 is activated to create suction through the sample flow path and reference solution is pumped through reference line 67. In order to flush the flow path, the probe is retracted by drive motor 22, so that its inlet opening 21 is positioned in the flush-fluid chamber of septum assembly 24. Flush fluid therefore is drawn through the flow path and out the waste outlet 28, cleaning the flow path.

When the analyzer is idle, pump 29 is controlled to maintain a gas/liquid interface at detector 103, thereby maintaining the electrolyte and pH electrodes in a liquid environment while maintaining the PCO$_2$ and PO$_2$ electrodes in a gas environment.

To standardize the electrodes the probe inlet is introduced sequentially, under the control of computer 130 and motor 22, into each septum assembly cavity; with the probe positioned in a given cavity, the computer 130 controls pinch valve motor control 64 or solenoid valves 46 and 46' to open the desired standard fluid (liquid or gas) to the septum assembly. Other standards are sealed by pinch valve 51 and solenoid valves 46 and 46', to provide additional assurance against contamination. Standardizing with liquids $E_A$, $E_B$, pH$_A$, and pH$_B$ is accomplished by flowing a standard through the flow path and then holding it there by appropriate control of pump 29 in response to liquid positions indicated by the air detectors. Standardizing with $G_A$ and $G_B$ is accomplished by flowing those standards along the flow path. Electrical signal values for each standard are recorded and stored by storage means in computer 130 for later comparison with sample signal values. Valves 46 and 46' each comprise dual solenoid valves to allow a metered flow of standardizing gas under the control of computer 130.

Standardization being complete, when analysis is required, the probe is fully extended to draw sample solution through the flow path, without contamination from standards. Signals representative of each measured sample characteristic are generated and transferred to computer 130 for comparison with standard signals thus establishing a value for each characteristic that is fed to output apparatus—i.e., C.R.T. display 12 and tape printout 14. With the exception of the hematocrit measurement, the details of the apparatus for generating standard and sample signals, for comparing those signals, and for calculating values for sample characteristics are well known and need not be repeated here.

FIG. 13 shows other aspects of the electronic components and their connection to computer 130. Specifically, in FIG. 13, inputs to computer 130 are provided from keypad 16 and from multiplexer 183 via filter 187 and A/D converter 188. The computer provides output to probe motor control 222, pinch valve motor controller 64, sample preheater controller 160', air heater and blower controller 66', and solenoid valves 46 and 46'. Also, computer 130 provides output to CRT screen 12 and printer 14.

OTHER EMBODIMENTS

Other embodiments are within the following claim. For example, other blood components or additional blood components can be sensed by the analyzer. Other electrolytes such as [Cl$^-$] can be used as a surrogate for hematocrit. In that case, suitable [Cl$^-$] concentrations of standardizing solutions $E_A$ and $E_B$ are 110 mM and 60 mM, respectively. In that case, 41 in FIG. 12A would be a [Cl$^-$] sensing electrode. In place of the electrode isolating circuitry described above, the electrodes could be directly coupled to an AC conductivity measuring circuit with a local ground (e.g. in the preheater).

We claim:

1. A method for determining the hematocrit value of a blood sample by:
   (a) providing apparatus comprising a liquid flow path, means in the flow path for generating an electrical signal representative of the electrical conductivity of liquid in the Path, and means in the flow path for obtaining an electrical signal representative of the concentration of at least one ion species in liquid in the flow path;
   (b) introducing standardizing solution in the flow Path having a known concentration of said ion species and having a conductivity indicative of a known equivalent hematocrit value, and obtaining a signal representative of said standardizing solution conductivity and obtaining a signal representative of said known ion species concentration;
   (c) either before or after introducing the standardizing solution, introducing the sample in the flow path and obtaining an electric signal representative of the sample conductivity and an electric signal representative of the sample ion-species concentration; and (e) deriving a tentative sample hematocrit value responsive to the sample conductivity signal, with reference to said standardizing conductivity signal and to said known standardizing equivalent hematocrit value; and (f) correcting said tentative sample hematocrit value with reference to said sample and standardizing ion concentration signals and to said known ion concentration value.

2. The method of claim 1 wherein said method further comprises providing, from time to time, an external validation of said apparatus by introducing a control solution in said flow path, said control solution having a known ion species concentration, and a conductivity representative of a known equivalent hematocrit level.

3. The method of claim 2 wherein said control solution equivalent hematocrit level is within a physiologically normal range, and said control solution ion species concentration is within a physiologically normal range.

4. The method of claim 2 wherein said control solution comprises an ion activity enhancing agent.

5. The method of claim 2 wherein said agent is a polyol.

6. The method of claim 5 wherein said polyol is selected from glycerol and polyalkyl glycols.

7. The method of claim 1 or claim 2 wherein said conductivity obtaining step comprises:

(a) providing electrodes in said flow path coupled to a constant amplitude AC circuit via a transformer;

(b) applying an AC signal to said electrodes from said circuit via said transformer; and (c) detecting impedance reflected in said AC circuit.

8. The method of claim 1 or claim 2 wherein said method comprises performing the following steps in any order:

(a) obtaining said electrical signals representative of standardizing conductivity and standardizing ion concentration;

(b) storing signals representative of said known standardizing equivalent hematocrit value and said known standardizing ion concentration value;

(c) obtaining said electrical signals representative of sample ion concentration and sample condutivity;

(d) comparing said sample and said standardizing ion concentration signals with reference to said stored known standardizing concentration value signal to derive a signal representative of sample ion concentration value;

(e) comparing said sample and said standardizing conductivity signals with reference to said stored standardizing hematocrit value signal to derive a signal representative of a tentative sample hematocrit value;

(f) correcting said tentative sample hematocrit value signal with reference to said sample ion concentration signal and said stored standardizing ion concentration value signal.

9. The method of either claim 1 or claim 2 wherein said ion species is $Na^+$ or $Cl^-$.

10. Apparatus for determining hematocrit value in a blood sample comprising: (1) means for providing a fluid flow path; (2) means in said flow path for providing an electrical signal representative of the conductivity of liquid passing along said flow path; (3) means in said flow path for providing a signal representative of the concentration of an ion species in liquid passing along said flow path; (4) means for introducing said blood sample into said flow path to obtain a signal representative of sample conductivity and of sample ion species concentration; (5) means for introducing into said flow path a standardizing solution having a known concentration of an ion species and having a conductivity representative of a known equivalent hematocrit value; (6) means for deriving a signal representative of a tentative sample hematocrit value from the sample conductivity signal, with reference to the standardizing conductivity signal and to the standardizing equivalent hematocrit value; and (7) means for correcting said tentative sample hematocrit value with reference to said standardizing and sample ion concentration signals and to said known standardizing ion concentration.

11. The apparatus of claim 10 wherein said apparatus comprises means for storing either said sample or said standardizing conductivity signal, and means for comparing said conductivity signals with reference to said known standardizing equivalent hematocrit value to generate a signal representative of said tentative sample hematocrit value.

12. The apparatus of claim 11 wherein said means for correcting said tentative sample hematocrit value signal comprises means for storing either said standardizing or said sample ion concentration signal and comparing said concentration signals with reference to said known standardizing ion concentration value.

13. The apparatus of claim 10 wherein said apparatus comprises at least two standardizing solutions, each of which has a conductivity indicative of a known equivalent hematocrit value and a known ion concentration.

14. The apparatus of claim 10 wherein said ion species is $Na^+$ or $Cl^-$.

15. The apparatus of claim 10 wherein said means for providing an electrical signal representative of conductivity comprises electrodes in said flow path, a constant amplitude AC circuit coupled to said electrodes via a transformer, and means for detecting reflected impedance in said AC circuit.

16. The apparatus of claim 15 wherein said means for providing a signal respresentative of conductivity comprises: (1) a first transformer for coupling said AC circuit to said electrodes; (2) a second transformer for maintaining constant amplitude in said AC circuit; and (3) means establishing a loop, connected between said electrodes, comprising means connected in said loop between said electrodes and said second transformer to compensate for inherent capacitance at the electrode/sample interface.

17. The apparatus of claim 16 wherein said apparatus comprises an ion-species sensitive electrode positioned in said flow path and connected via an electrical circuit to the input of a multiplexer, said impedance detecting means also being connected to the input of said multiplexer, said multiplexer having an output means connected via an analog-to-digital converter to a means for storing and comparing signals, and to said means for correcting sample conductivity.

18. A control solution kit for evaluating apparatus that determines a tentative level for the hematocrit of a blood sample by determining the sample conductivity and correcting said tentative level with reference to a sample ion species concentration level, said kit comprising an aqueous solution comprising said ion species and an ion activity enhancing agent, said solution having a known concentration of said ion and a known equivalent hematocrit value.

19. The kit of claim 18 wherein said ion species is $Na^+$ or $Cl^-$.

20. The kit of claim 19 wherein said agent is a polyol.

21. The kit of claim 19 wherein said polyol is selected from glycerol and polyalkyl glycols.

22. The kit of claim 18 wherein said ion concentration and said equivalent hematocrit level are within physiologically normal ranges.

23. Apparatus for determining the concentration of a blood sample component comprising means defining a flow path, means in said path for generating an electrical signal representative of said component concentration in fluids in said path, means for introducing at least two standardizing solutions in said flow path, and means for comparing the sample concentration signal with the standardizing concentration signals wherein said apparatus further comprises a septum assembly connected to said flow path means and to said standardizing fluid introducing means, said septum assembly comprising:
(a) chamber-defining members, said members defining a plurality of chambers, said members being permanently attached to each other; and
(b) flexible septa positioned between said chambers, each said septum having a slit, said slits being aligned to sealably receive therethrough an elongated probe connected to said flow path, each said chamber being connected to a said standardizing fluid introducing means, said septum assembly being removably attached as a unit to said apparatus, said apparatus including means for releasably attaching said septum assembly in position to receive said probe through said slits.

24. The apparatus of claim 23 wherein said releasable attaching means comprises a post on the base of said septum assembly and a means on said apparatus for cooperatively engaging said post, said engaging means comprising a pair of elongated resilient spring means spaced to receive and releasably engage said post therebetween.

25. The apparatus of claim 23 wherein each said chamber-defining members comprises an inlet means, and said standardizing fluid introducing means comprises an integral standardizing-fluid-flow-path manifold connector having a plurality of outlets, each of which is positioned and sized to removably seal to a said inlet means.

26. The apparatus of claim 25 wherein each said inlet means comprises a cylindrical inlet positioned in a recess in said chamber-defining member, and said manifold connector is cooperatively sized and shaped to fit within said recesses.

27. A septum assembly comprising means for removable attachment to apparatus for measuring the concentration of blood sample components, said assembly comprising chamber-defining members defining a plurality of chambers, said members being permanently attached to each other, and flexible septa positioned between said chambers, each said septa having a sealable slit, said slits being aligned, each said septum assembly chamber comprising means for connection to a standardizing fluid source, said septum assembly further comprising a means for releasable attachment as a unit to said analyzer in position to sealably receive through said aligned slits a hollow elongated analyzer probe.

28. The septum assembly of claim 27 wherein said releasable attachment means comprises a post on the base of said septum assembly configured to cooperatively engage a pair of elongated resilient spring means on said concentration measuring apparatus, spaced to receive and releasably engage said post therebetween.

29. The septum assembly of claim 27 wherein each said chamber-defining member comprises an inlet means and means surrounding said inlet means for receiving a manifold connector.

30. The septum assembly of claim 27 wherein each said septa comprises an annular ridge positioned radially outwardly of, and concentrically with, said slit to seal against a said chamber-defining member.

* * * * *

UNITED STATES PATENT AND TRADEMARK OFFICE
CERTIFICATE OF CORRECTION

PATENT NO. : 4,686,479

DATED : August 11, 1987

INVENTOR(S) : Chung C. Young et al.

It is certified that error appears in the above-identified patent and that said Letters Patent is hereby corrected as shown below:

Column 1, line 35, "("[Ca+]")" is corrected to read --("[Ca++]")--.

Column 6, line 56, "$G_A$", first occurrence, is corrected to read --$G_B$-- and "(1)" is corrected to read --(2)--.

Column 12, line 33, "Sutiable" is corrected to read --Suitable--.

Column 14, claim 1, line 54, "Path" is corrected to read --path--.

Column 14, claim 1, line 59, "Path" is corrected to read --path--.

Column 15, claim 8, line 45, "condutivity" is corrected to read --conductivity--.

Signed and Sealed this

Seventh Day of September, 1993

Attest:

BRUCE LEHMAN

Attesting Officer

Commissioner of Patents and Trademarks